United States Patent
Lue et al.

(10) Patent No.: US 8,927,242 B2
(45) Date of Patent: Jan. 6, 2015

(54) TREATMENT AND PROPHYLAXIS FOR OBSESSIVE COMPULSIVE DISORDER

(71) Applicant: NuBiome, Inc., Mountain View, CA (US)

(72) Inventors: Brian C. Lue, Mountain View, CA (US); Fredrick C. Westall, Temecula, CA (US)

(73) Assignee: NuBiome, Inc., Mountain View, CA (US)

( * ) Notice: Subject to any disclaimer, the term of this patent is extended or adjusted under 35 U.S.C. 154(b) by 0 days.

(21) Appl. No.: 13/886,424

(22) Filed: May 3, 2013

(65) Prior Publication Data

US 2013/0302296 A1 Nov. 14, 2013

Related U.S. Application Data

(60) Provisional application No. 61/645,246, filed on May 10, 2012.

(51) Int. Cl.
*C12P 1/04* (2006.01)
*A61K 35/74* (2006.01)
*A61K 38/48* (2006.01)

(52) U.S. Cl.
CPC ............. *A61K 35/74* (2013.01); *A61K 38/4886* (2013.01); *A61K 38/482* (2013.01); *A61K 35/744* (2013.01); *Y10S 435/885* (2013.01)
USPC .......................................... 435/170; 435/885

(58) Field of Classification Search
None
See application file for complete search history.

(56) References Cited

U.S. PATENT DOCUMENTS

| 8,383,101 | B2 * | 2/2013 | Olmstead ...................... 424/94.2 |
| 2011/0081320 | A1 | 4/2011 | Westall et al. | |
| 2011/0256179 | A1 * | 10/2011 | Roos et al. ................. 424/243.1 |

OTHER PUBLICATIONS

Y.S. Chen et al. "Genetic characterization and physiological role of endopeptidase O from *Lactobacillus helveticus* CNRZ32" App. Environ. Microbiol., 64 pp. 3411-3415 (1998).
R.C. Dale et al. "Incidence of anti-brain antibodies in children with obsessive-compulsive disorder" in Brit. J. Psychology, 187 pp. 314-319 (2005).
Y.S. Chen et al. "Identification and characterization of *Lactobacillus helveticus* Pep O2 an endopeptidase with post proline specificity" App. Environ. Microbiol., 69 pp. 1276-1282 (2003).
A. Beck "Interference by an alpha-hemolytic *streptococcus* of beta-hemolytic pathogenic streptococci" Inflammation, 4 pp. 463-465 (1979).
E. Grahn et al. "Interference of alpha-hemolytic streptococci isolated from tonsillar surface of beta-hemolytic streptococci (Streptococci pyrogenes)—a methodological study" Zbl. Bakr. Hyg I. Abt Orig A, 254 pp. 459-468 (1983).
S. Lakhan et al. "Nutritional therapies for mental disorders" Nutrition Journal, 7:2 pp. 1-8 (2008).
K. Kanamaru et al. "Overexpression of the PepF Oligopeptidase inhibits sporulation initiation in *Bacillus subtilis*" J. Bacteriol., 184 pp. 43-50 (2002).
R.C. Dale "Post-streptococcal autoimmune disorders of the central nervous system" Dev. Med. & Child Neurology, 47 pp. 785-791 (2005).
T. Urano et al. "The profibrinolytic enzyme subtilisin NAT purified from *Bacillus subtilus* cleaves and inactivates plasminogen activator inhibitor type 1" J. Biol. Chem., 276 pp. 24690-24696 (2001).
H. Lilja et al. "Alpha-streptococci inhibiting beta-streptococci group A in treatment of recurrent streptococcal tonsillitis" Otorhinolaryngol., 476 pp. 168-171 (1992).
R.L. Hsu et al. "Amyloid-degrading ability of nattokinase (subtilisin) from *Bacillus subtilus* natto" J. Agricul. Food Chem., 57 pp. 503-508 (2009).
E. Sanders "Bacterial interference. I Its occurrence among the respiratory tract flora. A characterization of inhibition of group A streptococci by viridans streptococci" Infect. Dis., 120 pp. 698-707 (1969).
E. Grahn et al. "Bacterial interference in the throat flora during a streptococcal tonsillitis outbreak in an apartment house area" Zbl. Bakt. Hyg A, 256 pp. 72-79 (1983).
V. Monnet et al. "Biochemical and Genetic Characterization of PepF, an Oligopeptidase from *Lactococcus lactis*" J. Biol. Chem., 269 pp. 32070-32076 (1994).
S.H. Chao et al. "Characterization of a novel Pep-F-like oligopeptidase secreted by *Bacillus amyloliquefaciens*" App. Environ. Microbiol., 72 pp. 968-971 (2006).
C. Christensson et al. "Cloning and expression of an oligopeptidase, PepO, with novel specificity from *Lactobacillus rhamnosus* HN001" App. Environ. Microbiol., 68 pp. 254-262 (2002).
I. Mierau et al. "Cloning and sequencing of the gene for a Lactococcal endopeptidase, an enzyme with sequence similarity to mammalian enkephalinase" J. Bacteriol., 175 pp. 2087-2096 (1993).
C. Janer et al. "Enzymatic ability of *Bifidobacterium animalis* subsp. lactis to hydrolyze milk proteins: Identification and Characterization of Endopeptidase O" in App. Environ. Microbiol., 71 pp. 8460-8465 (2005).

* cited by examiner

*Primary Examiner* — Allison Fox
*Assistant Examiner* — Yvonne Pyla
(74) *Attorney, Agent, or Firm* — Michael B. Einschlag

(57) ABSTRACT

An embodiment is a method of preventing, mitigating or treating Pediatric Autoimmune Neuropsychiatric Disorders Associated with Streptococcal Infections (PANDAS) that includes administering an effective amount of a medicament comprised of *Streptococcus oralis* 89a to a human to prevent, mitigate or treat PANDAS.

5 Claims, No Drawings

TREATMENT AND PROPHYLAXIS FOR OBSESSIVE COMPULSIVE DISORDER

This patent application relates to U.S. Provisional Application No. 61/645,246 filed May 10, 2012 from which priority is claimed under 35 USC §119(e), and which provisional application is incorporated herein in its entirety.

BACKGROUND

Many mental illnesses are caused by autoimmune reactions to nervous tissue and neurological signaling chemistries and their receptors. Examples of such diseases are Pediatric Autoimmune Neuropsychiatric Disorders Associated with Streptococcal Infections (PANDAS). PANDAS cause some Obsessive Compulsive Disorder (OCD) and tic disorders. Researchers have reported finding antibodies that react to the brain's basal ganglia in people suffering from PANDAS (see an article entitled "Incidence of anti-brain antibodies in children with obsessive-compulsive disorder" by Dale et al. in *Brit J. Psychology* 187: 314-319, 2005). Researchers have also reported that the production of antibodies that react to these emotional and movement brain structures (i.e., the basal ganglia) is caused, or stimulated, by cross-reactions to antigens arising from Group A Streptococcal (GAS) bacteria (see an article entitled "Post-streptococcal autoimmune disorders of the central nervous system" by R. C. Dale in *Dev. Med. & Child Neurology* 47: 785-791, 2005).

Present treatments for OCD have primarily included psychotherapy and use of drugs. Most commonly, the drugs used are antidepressants. Such drugs are prescribed because they are believed to increase the levels of serotonin in the brain. Examples of such drugs are Clomipramine, Fluvoxamine, Fluoxetine, Paroxetine and Sertraline. Present treatments for tic disorders include prescription of atypical neuroleptics such as risperidone, ziprasidone, haloperidol, pimozide and fluphenazine (see an article entitled "Nutritional therapies for mental disorders" by Lakhan et al. in *Nutrition Journal* 7:2 1-8, 2008). A problem with these approaches is that since certain PANDAS types of OCD and tic disorders are caused by an autoimmune reaction, the aforementioned drugs do not address the root cause of the problem, namely, an immune reaction to the nervous system.

SUMMARY

One or more embodiments of the present invention address the root cause of the above-identified problem, namely, an autoimmune response against basal ganglia structures in the brain. In order to reduce antibody production, in accordance with one or more of such embodiments, bacteria and/or enzymes that interfere with and/or reduce the population of Group A Streptococcal (GAS) bacteria are used. It is believed that GAS bacteria create cross-reacting antibodies to emotional brain structures such as the basal ganglia (see an article entitled "Interference by an alpha-hemolytic *streptococcus* of beta-hemolytic pathogenic *streptococcus*" by A. Beck in *Inflammation* 4: 463-465, 1979 and an article entitled "Bacterial interference. Its occurrence among the respiratory tract flora. A characterization of inhibition of group A *streptococci* by *viridans streptococci*" by E. Sanders in *Infect. Dis.* 120: 698-707, 1969). In accordance with one or more embodiments, an effective amount of a medicament comprised of one or more suitable bacteria and/or one or more suitable enzymes is administered to a person (or other mammal) to prevent, mitigate or treat PANDAS. An example of one suitable bacterium is, but is not limited to, *Streptococcus oralis* (formerly called *Streptococcus sanguis*) 89a. *Streptococcus oralis* 89a is commercially available from Probac, AB (Umea, Sweden).

DETAILED DESCRIPTION

One or more embodiments of the present invention address the root cause of the above-identified problem, namely, an autoimmune response against basal ganglia structures in the brain. To reduce antibody production, and hence, the autoimmune response thereto, in accordance with one or more of such embodiments, bacteria that interfere with and/or reduce the population of Group A Streptococcal (GAS) bacteria before they encounter the immune system are used. It is believed that GAS bacteria create cross-reacting antibodies to emotional brain structures such as the basal ganglia.

In accordance with one or more embodiments, an effective amount of a medicament comprised of one or more suitable bacteria is administered to a person (or other mammal) to prevent, mitigate or treat PANDAS. An example of one such bacterium is, but is not limited to, *Streptococcus oralis* (formerly called *Streptococcus sanguis*) 89a (*S. oralis* 89a). *Streptococcus oralis* 89a is an alpha-hemolytic streptococci (AHS) that is a normal, non-pathogenic inhabitant of the human throat. AHS is the predominant species in the upper airway among healthy individuals; children as well as adults. It is one of the main components of human upper airway. Its traits include adherence to throat epithelial tissue, an ability to persist in the throat, and an ability to interfere with different serotypes of group A *streptococci* (GAS) in vitro and in vivo. *Streptococcus oralis* 89a is commercially available from Probac, AB of Umea, Sweden. An effective amount of *S. oralis* 89a contained in the medicament is in a range from about $1 \times 10^5$ to about $1 \times 10^{12}$ colony forming units (CFU) of *S. oralis* 89a per day.

In accordance with one or more such embodiments, an effective amount of a medicament comprised of *Streptococcus oralis* 89a bacteria (*S. oralis* 89a) is administered to a person (or other mammal) suffering from PANDAS. An effective amount of *S. oralis* 89a contained in the medicament is in a range from about $1 \times 10^5$ to about $1 \times 10^{12}$ colony forming units (CFU) of *S. oralis* 89a per day.

Because immunogens, mimics and/or antigens for a disease can stimulate the production of antibodies to the nervous system, further embodiments include medicaments which: (a) contain one or more enzymes capable of breaking down immunogens, mimics and/or antigens—especially those hard to digest proline containing peptides; and/or (b) contain one or more live and/or dead bacteria or portions of such bacteria capable of producing one or more enzymes capable of breaking down immunogens, mimics and/or antigens—especially those hard to digest proline containing peptide mimics, immunogens and/or antigens. In particular, one or more embodiments comprise: (a) the use of one or more such enzymes by themselves or in concert with *S. oralis* 89a; and/or (b) the use of one or more bacteria capable of producing one or more such enzymes that break down these mimics, immunogens and/or antigens by themselves or in concert with *S. oralis* 89a. Examples of suitable such enzymes include, but are not limited to, oligopeptidase F (PepF) (see an article entitled "Characterization of a novel Pep-F-like oligopeptidase secreted by *Bacillus amyloliquefaciens*" by Chao et al. in *Applied Environ. Microbiol.* 72: 968-971, 2006; an article entitled "Overexpression of the PepF Oligopeptidase inhibits sporulation initiation in *Bacillus subtilis*" by Kanamaru et al. in *J. Bacteriol.* 184: 43-50", 2002; and an article entitled "Biochemical and Genetic Characterization of PepF, an Oligopeptidase from *Lactococcus lactis*" by Monnert et al. in *J. Biol. Chem.* 269: 32070-32076, 1994); endopeptidase O (PepO) (see an article entitled "Cloning and expression of an oligopeptidase, PepO, with novel specificity from *Lactobacillus rhamnosus* HN001" by Christensson et al. in *Applied Environ. Microbiol.* 68: 254-262, 2002; an article entitled "Enzymatic ability of *Bifidobacterium animalis* subsp. Lactis to hydrolyze milk proteins: Identification and Characterization of Endopeptidase O" by Janer et al. in *Applied Environ. Microbiol.* 71: 8460-8465, 2005; an article entitled "Genetic characterization and physiological role of endopeptidase O from *Lactobacillus helveticus* CNRZ32" by Chen et al. in *Applied Environ. Microbiol.* 64: 3411-3415, 1998; and an article entitled "Cloning and sequencing of the gene for a Lactococcal endopeptidase, an enzyme with sequence similarity to mammalian enkephalinase" by Mierau, et al. in *J. Bacteriol.* 175: 2087-2096, 1993); endopeptidase O2 (PepO2) (see an article entitled "Identification and characterization of *Lactobacillus helveticu* Pep O2 an endopeptidase with post proline specificity" by Chen et al. in *Applied Environ. Microbiol.* 69: 1276-1282, 2003) and subtilisin (see an article entitled "Amyloid-degrading ability of nattokinase (subtilisin) from *Bacillus subtilus* natto" by Hsu et al. in *J. Agricul. Food Chem.* 57: 503-8, 2009). One of ordinary skill in the art can readily purchase these enzymes commercially or fabricate them using methods that are well known to those of ordinary skill in the art. In accordance with one or more such embodiments, an effective amount of a medicament comprised of one or more enzymes capable of breaking down immunogens, mimics and/or antigens is administered to a human (or other mammal) suffering from PANDAS. Examples of such enzymes include, but not limited to, PepF, PepO, PepO2 and subtilisin. In addition, in accordance with one or more further embodiments, an effective amount of a medicament comprised of one or more bacteria capable of producing one or more enzymes capable of breaking down immunogens, mimics and/or antigens is administered to a human (or other mammal) suffering from PANDAS. Examples of such enzymes include, but not limited to, PepF, PepO, PepO2 and subtilisin.

In accordance with one or more further such embodiments, a medicament comprised: (a) of an effective amount of one or more enzymes is administered to a human (or other mammal) to prevent/treat/cure PANDAS; and/or (b) of an effective amount of one or more bacteria capable of producing an effective amount of one or more enzymes is administered to a human (or other mammal) to prevent/treat/cure PANDAS. Further, in accordance with one or more further such embodiments: (a) an effective amount of the one or more enzymes is an amount of the one or more enzymes (for example, in sufficient concentration) that is effective in destroying or deactivating immunogens, mimics or antigens that cause or exacerbate PANDAS; and/or (b) an effective amount of the one or more bacteria capable of producing one or more enzymes is an amount of the one or more bacteria (for example, in sufficient concentration) that is effective in producing an amount of the one or more enzymes effective in destroying or deactivating immunogens, mimics or antigens that cause or exacerbate PANDAS.

In accordance with one or more embodiments, an effective amount of oligopeptidase F (PepF) administered will depend upon the severity of the disease process (the PepF may be administered one or more, preferably three, doses daily). However, an effective amount of PepF (for example, in sufficient concentration) is in a range from about 20 units/day to about 200 units/day, where the definition of a unit is an amount of PepF required to cleave one micromole of bradykinin at a pH of 8.0 and a temperature of 40° C.

PepF belongs to the M3 metalloprotease family. While most bacterial PepFs are cytoplasmic endopeptidases, some are secreted; for example, the enzyme from *Bacillus amyloliquefaciens*. PepF has been seen in a variety of bacterial genuses including, *Lactococcus* and *Bacillus* and in *Bacillus subtilis*. In accordance with one or more embodiments, a medicament comprised of an effective amount of a non-pathogenic microorganism and/or its spores (that are capable of providing PepF) is administered to a patient to treat/cure PANDAS. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gasseri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), *Campylobacter subtilisis*, and *Oenococcus oeni* and their various strains. An effective amount of the microorganism and/or its spores is an amount that is effective to cause destruction or deactivation of mimics, immunogens and/or antigens that cause or exacerbate PANDAS. In accordance with one or more such embodiments, an effective amount is from about 100 thousand CFU to about 600 billion CFU per dose, where the dose is administered about one or more times per week, or as often as about one to about three times daily.

In accordance with one or more embodiments, a medicament comprised of an effective amount of parts of, or entire broken up, microorganisms and/or their spores (that are capable of providing PepF) is administered to a patient to treat/cure PANDAS. Parts of the microorganisms and/or spores can be separated and selected, using any one of a number of methods that are well known to those of ordinary skill in the art, for their bioactive properties to help ensure and improve the rate of the destruction or deactivation of mimics, immunogens and/or antigens that cause or exacerbate PANDAS and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gasseri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), and *Oenococcus oeni* and their various strains. An effective amount of the parts of, or entire broken up, microorganisms and/or their spores is an amount sufficient to cause destruction or deactivation of mimics, immunogens and/or antigens that cause or exacerbate PANDAS. In accordance with one or more such embodiments, an effective amount of parts or entire broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more embodiments, an effective amount of endopeptidase O (PepO) administered will depend upon the severity of the disease process (the PepO may be administered in one or more, and preferably three, doses daily). However, an effective amount is in a range from about 20 units/day to about 200 units/day, where the definition of a unit is an amount of PepO required to cleave one micromole of bradykinin at a pH of 6.0 and a temperature of 25° C.

In accordance with one or more embodiments, a medicament comprised of an effective amount of a non-pathenogenic microorganism and/or its spores (that are capable of providing PepO) is administered to a patient to prevent/treat/cure PANDAS. PepO is found in a large range of bacterial systems. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antrii, Lactobacillus paracasei, Lactobacillus ruminis, Lactococcus lactis, Bifidobacterium dentium, Bifidobacterium longum, Bifidobacterium adolescentis, Bifidobacterium animalis*, and *Oenicoccus oeni* and their various strains. An effective amount of the microorganism and/or its spores is an amount that is effective to cause destruction or deactivation of mimics, immunogens and/or antigens that cause or exacerbate PANDAS. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entire broken up, microorganisms and/or their spores (that are capable of providing PepO) is administered to a patient to prevent/treat/cure PANDAS. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate PANDAS and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antri, Lactobacillus paracasei, Lactobacillus ruminis, Lactococcus lactis, Bifidobacterium dentium, Bifidobacterium longum, Bifidobacterium adolescentis, Bifidobacterium animalis*, and *Oenicoccus oeni* and their various strains. An effective amount of the parts of, or entire broken up, microorganisms and/or their spores is an amount sufficient to cause destruction or deactivation of mimics, immunogens and/or antigens that cause or exacerbate PANDAS. In accordance with one or more such embodiments, an effective amount of parts or entire broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more further embodiments, a medicament comprised of an effective dose of endopeptidase O2 (PepO2) from *Bifidobacterium animalis* subsp *lactis* is administered to a patient to prevent/treat/cure PANDAS. Such PepO2 will destroy potential mimics, immunogens and/or antigens prior to immune activation.

In accordance with one or more embodiments, an effective amount of endopeptidase O2 (PepO2) administered will depend upon the severity of the disease process (the PepO2 may be administered in one or more, and preferably three, doses daily). However, an effective amount is in in a range from about 20 units/day to about 200 units/day, where the definition of a unit is an amount of PepO2 required to cleave one micromole of BCN (f193-209) at a pH of 6.5 and a temperature of 25° C.

In accordance with one or more embodiments, a medicament comprised of an effective amount of a non-pathenogenic microorganism and/or its spores (that are capable of providing PepO2) is administered to a patient to treat/cure PANDAS. In accordance with one or more such embodiments, the microorganism and spores include, for example and without limitation, *Lactococcus lactis cremoris, Lactobacillus helveticus*, and *Lactobacillus johnsonii* and their various strains. An effective amount of the microorganism and/or its spores is an amount that is effective to cause destruction or deactivation of mimics, immunogens and/or antigens that cause or exacerbate PANDAS. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entire broken up, microorganisms and/or their spores (that are capable of providing PepO2) is administered to a patient to treat/cure PANDAS. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate PANDAS and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, *Lactococcus lactis cremoris, Lactobacillus helveticus*, and *Lactobacillus johnsonii* and their various strains. An effective amount of the parts of, or entire broken up, microorganisms and/or their spores is an amount sufficient to cause destruction or deactivation of mimics, immunogens and/or antigens that cause or exacerbate PANDAS. In accordance with one or more such embodiments, an effective amount of parts or entire broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more embodiments, an effective amount of subtilisin administered will depend upon the severity of the disease process (the subtilisin may be administered in one or more, preferably three, doses daily). However, an effective amount is in a range from about 2,000 fibrinolytic units/day to about 10,000 fibrinolytic units/day. In accordance with one or more further embodiments, a medicament comprised of an effective amount of a non-pathogenic microorganism and/or its spore that are capable of providing subtilisin is administered to a patient to treat/cure PANDAS. In accordance with one or more such embodiments, suitable microorganisms and spores include, for example, but not limited to, *Bacillus subtilis, Bacillus licheniformis*, and *Bacillus lentus* and their various strains. An effective amount of the microorganism and/or its spores is an amount that is effective to cause destruction or deactivation of mimics, immunogens and/or antigens that cause or exacerbate PANDAS. In accordance with one or more such embodiments, an effective amount is from about 100 thousand CFU to about 600 billion CFU per dose (CFU designates colony forming units), where the dose is administered about one or more times per week, or as often as about one to about three times daily. In accordance with one or more still further embodiments, a medicament comprised of an effective amount of parts of, or entire broken up, microorganisms and/or their spores capable of providing subtilisin, is administered to a patient to prevent/treat/cure PANDAS. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate PANDAS and/or to improve the effectiveness of enzymes in the gastrointestinal or respiratory tract in destroying or deactivating such mimics, immunogens and/or antigens.

In accordance with one or more embodiments, the above-described medicaments can be administered or delivered orally or via the nose or by suppository or by injection into a patient's gut (for example, and without limitation, by enema, endoscope, colonoscope, robotically actuated capsule, and so forth), to act as a prophylactic and/or to interfere with GAS in the upper respiratory and/or gastrointestinal tract to prevent/treat/cure PANDAS. As used herein, oral delivery includes, for example and without limitation, a capsule; a tablet; a chewable tablet/capsule; a spray; a gel, a liquid drink, a food, a powder, a gum, a candy, or cream containing the product. The term orally delivery includes sublingually, and on an absorbent substrate or adsorbent substrate. In accordance with one or more embodiments, a medicament can be administered rectally, where a rectal delivery mechanism includes, for example and without limitation, an enema, a fecal transplant, a gel, a cream, an ointment, or a suppository. A fecal transplant includes at least some of the following. First, a donor of feces is screened to look for parasites, pathogenic microorganisms, and to measure the kinds of microbes that are in the donor's feces. The donor's feces are also analyzed for chemicals having, for example, but not limited to, proteolytic activity. Next, the microbial and chemical measurements are compared against a set of requirements for a successful transplant, for example, but not limited to, the presence of bacteria or chemical activity that can destroy mimics, immunogens and/or antigens that cause or exacerbate PANDAS. Next, the donor's feces may be corrected for pH level by adding acids, bases, or appropriate buffering agents. Any imbalance of enzymes may be corrected by selecting an appropriate enzyme or pro- or co-enzyme producing microbe. A candidate microbe may be identified in the manner described below. Next, undesirable bacteria can be neutralized or killed. If the donor's feces do not have sufficient ability to destroy mimics, immunogens and/or antigens that cause or exacerbate PANDAS, then microorganisms that are capable of destroying mimics, immunogens and/or antigens that cause or exacerbate PANDAS, are added, in an effective amount, to the donor's feces prior to a fecal enema or around the time of the fecal enema to populate the sick person's gastrointestinal tract.

In accordance with one or more embodiments, the above-described medicaments can be administered transdermally, where a transdermal delivery mechanism includes, for example and without limitation, a skin patch, a spray, a gel, a cream, an ointment or a bath. In accordance with one or more embodiments, the above-described medicaments can be administered intravenously, where intravenous delivery includes, for example and without limitation, injection of the medicament mixed into an intravenous solution. In accordance with one or more embodiments, the above-described medicaments can be administered by inhalation, where intravenous delivery includes, for example and without limitation, a nebulized powder inhaled by the nose or mouth.

In accordance with one or more such embodiments, treatment may range from about weekly to about daily, and be ongoing until symptoms of PANDAS have disappeared.

The following describes methods for preparing useful microorganisms. Fermentation: As an example, microorganism *Bacillus subtilis* Natto produces the endoprotease subtilisin. Fermentation additives may be added to a culture of the microorganisms to enhance: production of microorganisms, ability of the microorganisms to survive in the gastrointestinal tract, ability of the microorganisms to adhere to the gastrointestinal tract, ability of the microorganisms to secrete desired proteases, ability of the microorganisms to secrete chemicals to enhance survival of proteases, ability of the microorganisms to secrete chemicals to enhance effectiveness of desired proteases, and ability of the microorganisms to secrete chemicals to interfere with undesired chemicals. Also, the amount and kinds of sugars, vitamins, amino acids, proteins and/or fats available to the microorganisms, prior to drying and forming a powder, affect their viability. Examples of useful sugars are, but are not limited to, sucrose, fructose, glucose, lactose, trehalose, raffinose, paliainose, lactulose, lactitol, xylitol, sorbitol, mannitol, malstose, dextrin and maltodextrin. Examples of useful anti-oxidants are, but are not limited to, ascorbic acid, glutathione and alpha-lipoic acid. Examples of useful amino acids or their salts are, but are not limited to, lysine, cysteine, glycine and glutamate. Examples of useful oils are, but are not limited to, butter, palm oil, nut oil, cocoa oil, rapeseed oil and soy bean oil. Examples of useful stabilizing ingredients are, but are not limited to, soybean oligosaccharides, frutooligosaccharides, galactooligosaccharides, galactosyl lactose, milk, milk powders, whey, whey protein concentrates, casein, casein hydrolysates, lactoferrin, lactoperoxidase, lactoglobulins, glymacropeptides, lacto-saccharides, glycomacropeptides, lacto-saccharides and lacto-lipids.

A chemical that inactivates an enzyme is, for example and without limitation, a serpin. Thus, it is desirable to inhibit serpins that inactivate proteases that destroy mimics, antigens, or immunogens that cause autoimmune disease. Also, protective agents such as, for example and without limitation, cryoprotectants or other chemicals such as gels, starches, polysaccharides, and/or sugars can be added to the culture to protect the microorganisms during the manufacturing processes.

Removing Liquid: When a powdered form of a microorganism is required, the microorganisms need to have liquid removed. One option, known to those of ordinary skill in the art, is to centrifuge the fermentation mixture to reduce the amount of liquid. Other options include, but are not limited to, settling and membrane filtration. This concentrates the microbes by separating them from their supernatant. As such, it allows for more microbes per kilogram of dried product to keep transportation and storage costs down and to deliver more microbes per capsule or pill. It also allows the microbes to be added as a concentrated powder to be mixed into a drink or sprinkled onto food. Centrifuging is beneficial when the supernatant does not contain substantial amounts of bioactive substances that the microbes cannot readily secrete or create in the gastrointestinal tract. However, if the supernatant has the bioactive substances for therapeutic effect, then centrifuging does not need to be performed if the microbes are still desired. In some cases, centrifuging or other separation processes, known to those of ordinary skill in the art, may be desired to obtain the bioactive substances, such as enzymes or bacteriocins, for delivery without the microbe. The following methods may also be used to separate microorganisms from supernatant: sedimentation, ultrafiltration and reverse osmosis.

Drying: This step dries the microorganisms as well as any available supernatant. The microorganisms can be dried with freeze-drying techniques, known to those of ordinary skill in the art, by placing the centrifuged microbes and residual supernatant, which form a slurry, onto trays and freezing them in a vacuum environment. After the slurry dries, it resembles a cake. The dried cake is then crushed, and the crushed powders are sieved to obtain the desired particle size distribution. This process of drying in bulk followed by crushing often kills many bacteria due to the thermal and mechanical stresses applied to the microbes. Another method of making a powder, known by those of ordinary skill in the art, is to spray dry the microorganisms. For this process the slurry is sprayed through a nozzle into a heated air environment. The incoming slurry can be heated or unheated. If the shear forces and temperatures that the microorganisms and/or enzymes experience during the heated spray drying process are too great, microorganisms will die or be damaged enough that the intended therapeutic effectiveness of the microorganism and/or enzyme will be diminished. To improve the yield and prevent damage to surviving microorganisms, an electrospray drying process can be used. Examples of manufacturers who make suitable electrospray drying equipment are Charge Injection Technology and Zoom Essence.

Blending: Other ingredients, such as but not limited to, dried proteases, microorganisms, protective sugars, polysaccharides, gums, oils, desiccants, anti-oxidants, and bacteriocins, can be added prior to or after the drying process. These ingredients will assist the microbes in surviving during storage as well as in passing to the target areas of the gastrointestinal tract. Also adding other ingredients is needed to reduce the dosage of concentrated microbial powders to the dosages required for delivery to the person.

Delivery: A powder can also be an acceptable delivery system especially when microorganisms do not need to be alive and where either their microbial parts or their secreted bioactive substances are effective against pathogens or for normalizing protease ratios. The powder can be consumed by adding the powder to a food or drink product. The powder containing the microorganisms and/or enzymes can be formulated by those of ordinary skill in the art into a drink that may contain for example, but not limited to, water, sweeteners, flavorings, colorants, anti-oxidants, vitamins, minerals, short-chain fatty acids, stimulants, mood-enhancers, teas, anti-inflammatories, and other bioactive ingredients. The powder can be consumed after sprinkling or pouring it over solid food or mixing into a liquid. The powder can be packaged into bulk containers such as a bag or can or into individual sachets for easy of carrying and single use dosing. To form a tablet, a powder containing the microbes and/or enzyme(s), excipients, and/or other bioactive substances are compressed into a mold in a tableting machine. The tablet can be coated with methods and processes known to those of ordinary skill in the art to prevent the premature dissolution of the product in the stomach to keep the microbes alive for delivery further down the gastrointestinal (GI) tract. Such coatings are designed by those of ordinary skill in the art to dissolve by time in the GI tract or more preferably by pH exposure as the pH along the GI tract is acidic in the stomach and the pH increases by the time the digested contents reach the large intestine. At the large intestine, the pH is approximately 7. Some examples known to those of ordinary skill in the art of a pH triggered coating are, but not limited to, Eudragit and shellac. The tablet can be designed by those of ordinary skill in the art to be consumed orally or inserted into the rectum or vagina as a suppository. To form a capsule, a powder containing the microorganisms, enzymes, excipients and/or other bioactive substances are directed into a capsule that can be made of materials known to those of ordinary skill in the art, but are not limited to, hardened gelatin or other polymer. The capsule can be coated by processes known to those of ordinary skill in the art to prevent the premature dissolution of the product in the stomach to keep the microorganisms alive and enzymes effective for delivery further down the GI tract. Such coatings known to those who are of ordinary skill in the art are designed to dissolve by time in the GI tract or more preferably by pH exposure. Some examples known to those of ordinary skill in the art of a pH triggered coating are, but not limited to, Eudragit and shellac. The capsule can be designed by those of ordinary skill in the art to be consumed orally or inserted into the rectum or vagina as a suppository. An alternate form of a capsule to contain the microorganisms, enzymes, excipients, and/or other bioactive substances is a gel capsule that can be made of materials and processes known to those of ordinary skill in the art.

For a liquid delivery system, the microorganisms and/or enzymes and bioactive substances can be introduced in a fermented liquid. That liquid can be in the form of cultured or non-cultured animal-based and/or plant-based milk such as, but not limited to, cow's, goat's, rice, almond, and/or soy milk. Alternatively, microorganisms and/or enzymes can added to a drink such, as but not limited to, a juice or formulated into a drink that may contain for example but not limited to water, sweeteners, flavorings, colorants, anti-oxidants, vitamins, minerals, short-chain fatty acids, stimulants, mood-enhancers, teas, anti-inflammatories and other bioactive ingredients. For a solid delivery system the microorganisms and/or enzymes and bioactive substances can be added to solid food in accordance with a number of methods that are well known to those of ordinary skill in the art. Examples of such food are, but are not limited to, candy, confectionery, chewing gum, energy bars, fermented/dried vegetables, fermented/dried meat, fermented/dried seafood, fermented/dried fruit, fermented/dried beans and frozen desserts. For a slurry delivery system the microorganisms and/or enzymes and bioactive substances can be added to slurry foods in accordance with a number of methods that are well known to those of ordinary skill in the art. Examples of such food are, but not limited to, yogurt, jams, jellies, gravies, gel shots, puddings, frozen desserts, salad dressings, syrups and spreads.

Embodiments of the present invention described above are exemplary, and many changes and modifications may be made to the description set forth above by those of ordinary skill in the art while remaining within the scope of the invention. As such, the scope of the invention should be determined with reference to the appended claims along with their full scope of equivalents.

What is claimed is:

1. A method of treating Pediatric Autoimmune Neuropsychiatric Disorders Associated with Streptococcal Infections (PANDAS) comprises:
   administering an effective amount of a medicament comprised of *Streptococcus oralis* 89a to a human to treat PANDAS.

2. The method of claim 1 wherein the medicament further comprises oligopeptidase F (PepF).

3. The method of claim 1 wherein the medicament further comprises endopeptidase O (PepO).

4. The method of claim 1 wherein the medicament further comprises endopeptidase O2 (PepO2).

5. The method of claim 1 wherein the medicament further comprises subtilisin.

* * * * *